United States Patent [19]

Suzuki

[11] 4,286,162
[45] Aug. 25, 1981

[54] SPEED CONTROL SYSTEM IN DENTAL RADIOGRAPHIC APPARATUS

[75] Inventor: Masakazu Suzuki, Kyoto, Japan

[73] Assignee: Kabushiki Kaisha Morita Seisakusho, Kyoto, Japan

[21] Appl. No.: 131,689

[22] Filed: Mar. 19, 1980

[30] Foreign Application Priority Data

Mar. 23, 1979 [JP] Japan .................................. 54/34590

[51] Int. Cl.³ .............................................. A61B 6/14
[52] U.S. Cl. ............................................... 250/439 P
[58] Field of Search .................................... 250/439 P

[56] References Cited
U.S. PATENT DOCUMENTS 4,039,837  8/1977  Ohta et al. ........................ 250/439 P
4,247,779  1/1981  Ciavattoni et al. ............... 250/439 P Primary Examiner—Alfred E. Smith
Assistant Examiner—T. N. Grigsby
Attorney, Agent, or Firm—Koda and Androlia

[57] ABSTRACT

The disclosure relates to a film feed speed control system in a dental radiographic apparatus for photographing the entire jaws, which apparatus has an X-ray generator and an X-ray film cassette holder mounted respectively at one end of a rotary arm of the apparatus and at the other end thereof. The system is designed to enable change in the magnification factor of an X-ray photograph by electrically and automatically increasing or decreasing the X-ray film speed independent of the X-ray generator.

10 Claims, 4 Drawing Figures

SPEED CONTROL SYSTEM IN DENTAL RADIOGRAPHIC APPARATUS

BACKGROUND OF THE INVENTION

1. Field of the Invention

This invention relates to an X-ray film feed speed control system in a dental radiographic apparatus for photographing the entire jaws.

2. Prior Art

In order to obtain a clear and sharp tomogram in the dental radiographic apparatus for photographing the entire jaws of the kind described, it is a general practice to change the rotatingly travelling speed of an X-ray generator moving along the dental arch, for example, with respect to the front teeth and to the back teeth to thereby control an X-ray dosage with respect to the front teeth and with respect to the back teeth. But it is necessary to synchronously change the speed of X-ray film feed in response to such control of X-ray dosage. To this end, it has heretofore been a general practice to provide a mechanism for changing an X-ray film feed speed in synchronism with the rotatingly travelling speed of the X-ray generator, increase the X-ray film speed when the moving speed of the X-ray generator is increased and the X-ray dosage with respect to each tooth is decreased, and reduce the X-ray film feed speed when the moving speed of the generator is decreased and the X-ray dosage with respect to each tooth is increased. But to facilitate diagnosis by making the desired region of the dental arch greater or smaller in magnification factor than the other regions thereof, it becomes necessary to change and control the X-ray film feed speed in the direction of higher or lower speed independent of the movement of the X-ray generator.

SUMMARY OF THE INVENTION

Accordingly, it is the primary object of this invention to provide an X-ray film speed control system in a dental radiographic apparatus for photographing an entire jaw, which system allows the X-ray film feed speed to be controllable independent of the movement of the X-ray generator.

In keeping with the principles of this invention, the objects are achieved by the unique structure where an X-ray generator and an X-ray film cassette holder are being moved around an object in a timed relation with each other in the state of the X-ray generator and the X-ray film cassette holder being located in a mutually opposed relation with the object interposed between the generator and the holder, an X-ray beam is irradiated on the object and the X-ray beam transmitting through the object is received by the X-ray film to make a tomogram of a required curved plane so as to provide a panoramic X-ray photograph of the entire jaw.

A detailed description will now be given, by way of example, of the invention with reference to the accompanying drawings illustrative of a preferred embodiment thereof.

DETAILED DESCRIPTION OF THE PREFERRED EMBODIMENT

Figure 1:
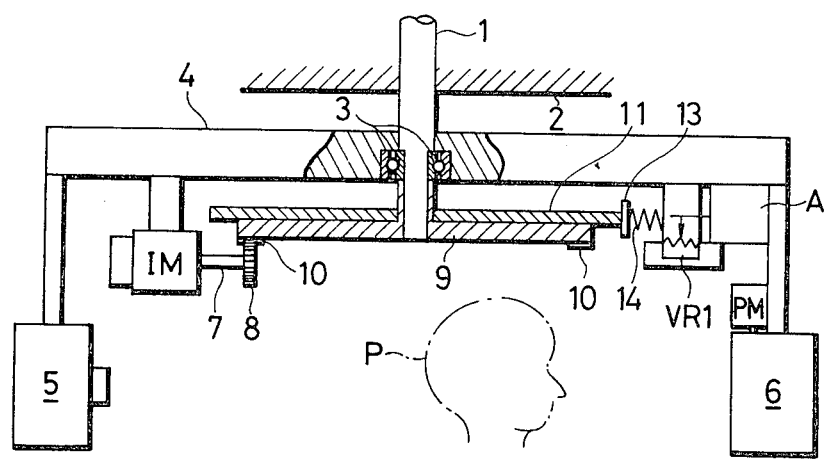
FIG. 1 is a schematic view of the mechanical component parts of the apparatus of the invention.
Figure 2:
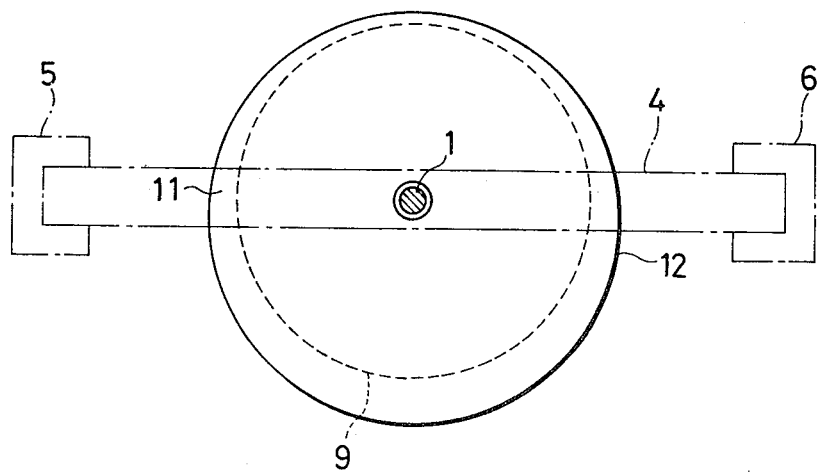
FIG. 2 is a plan view showing a relation between the center of the rotary arm and the cam plate.

In FIGS. 1 and 2, the numeral 1 designates a base shaft suspended from a support base 2, and a horizontal rotary arm (to be referred to as a rotary arm) 4 is horizontally rotatably suspended by the base shaft 1 through a bearing 3. The rotary arm is provided with an X-ray generator 5 and an X-ray film cassette holder 6 which are respectively held at one end of the rotary arm 4 and at the other end thereof in an opposed relation with each other in an angular phase difference of 180°. The arm is so constructed that when an X-ray photograph is taken, the arm is rotatingly moved within the same area of plane as that within which the X-ray generator 5 and X-ray film cassette holder 6 having an object P disposed therebetween encircle the object P and an X-ray film (not shown) is fed within the X-ray film cassette holder 6 in synchronism with the travelling speed of the arm. In order to rotate the arm 4, an induction motor IM is integrally mounted on the arm and a pinion 8 is fixedly mounted on an output shaft 7 of the motor IM. On the other hand, a receiving plate 9 is fixedly mounted on the base shaft 1 and a rack 10 is provided circumferentially of the circle described around the base shaft 1 on the underside of this receiving plate 9 and the rack 10 is in mesh with the pinion 8. Forced rotating force of the rotary arm 4 is induced by the pinion 8 being rotated on the rack 10 in meshing with each other by the rotation of the induction motor IM. Also, the arm 4 is provided with a pulse motor PM for feeding the X-ray film. Both motors IM and PM are electrically connected to each other by means G for converting the number of rotations of the arm drive motor IM into an electrical signal as well as by means of a rectifier circuit 18, DC voltage-pulse converter circuit 16 and a film feed motor drive circuit 17 as particularly shown in the circuitry in FIG. 3, and accordingly, if a variable resistor VR1 is fixedly mounted, the motor PM is synchronously changed in speed in proportion to the speed of rotation of the motor IM, namely the rotatingly travelling speed of the rotary arm 4 and of the X-ray generator 5, thereby controlling the feed speed of X-ray film.

But the invention is designed to vary a variable resistor VR1 automatically in the process of rotation of the rotating arm 4 and detect the X-ray irradiation position as a change in the resistance value of the variable resistor VR1 to thereby control the DC voltage-pulse converter circuit 16. Namely, the numeral 11 designates a cam plate detachably mounted on the top of a receiving plate 9 and the cam plate 11 is designed to variably control a transfer constant of a film feed motor drive control circuit A. Namely, the cam plate 11 has a circumferential cam face 12, and expansion and contraction of the plunger 13 in accordance with the rotation of the cam plate 11 successively change the resistance value of the variable resistor VR1 and cause the transfer constant of the circuit A to be changed, in turn, by the change in resistance value.

Figure 3:
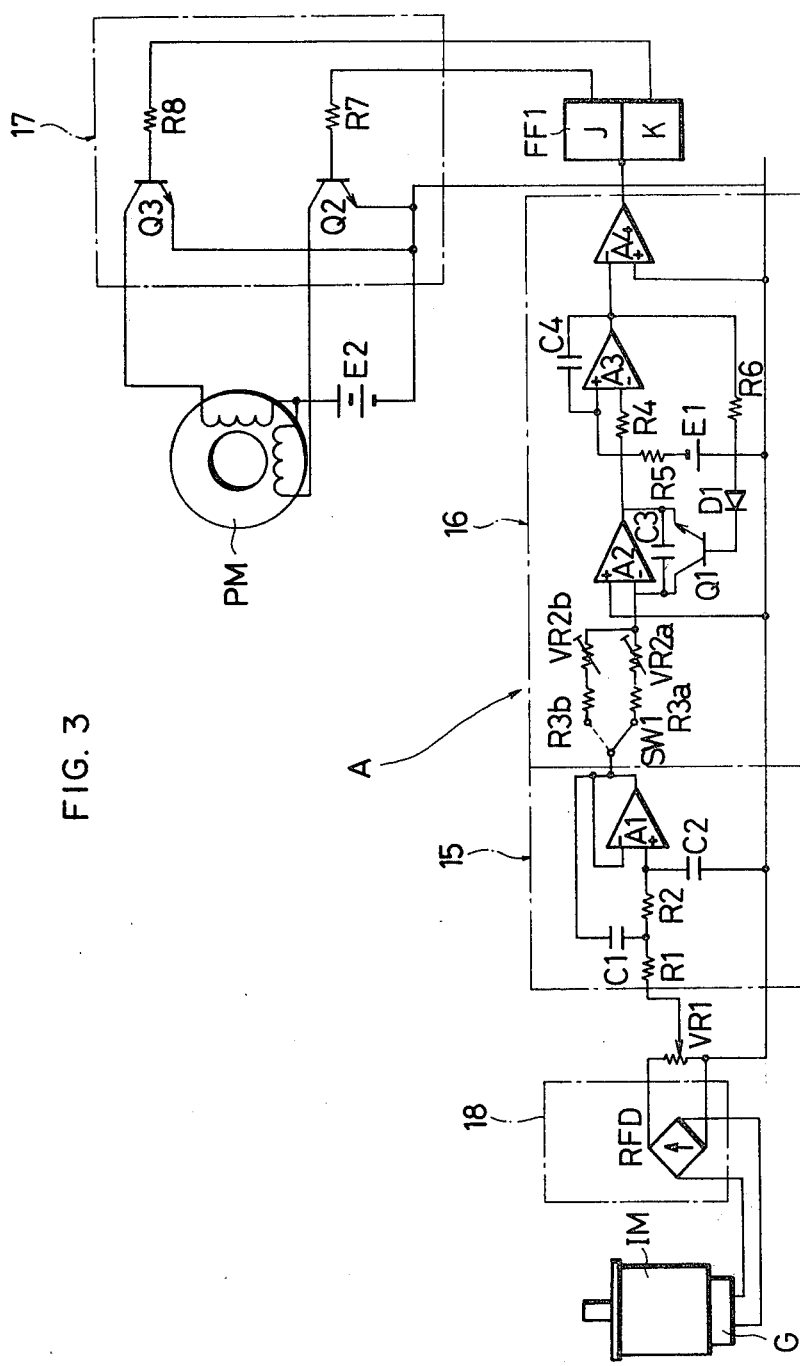
FIG. 3 is an electric circuit diagram.

In FIG. 3, a means for converting the number of rotations of the arm drive motor IM into an electrical signal is a tachogenerator connected directly to the output shaft 7 of the motor IM, the tachogenerator including AC voltage in proportion to the number of rotations of motor IM. The character RFD designates a rectifier for changing AC voltage into a pulse. The variable resistor VR1 connected directly to the rectifier RFD is variable in accordance with the rotation of the cam plate 11, and accordingly varies the feed speed of X-ray film in accordance with the number of rotations (speed of rotation) of motor IM, namely the travelling speed of the generator 5. The circuit including condensers C1 and C2, resistors R1 and R2 and an amplifier A1 composes low-pass filter circuit 15 and is intended to shut off high-frequency component contained in the above pulse. Also, the numeral 16 designates a DC voltage-pulse converter circuit which includes a Miller integration circuit, a comparator circuit and a buffer amplifier A4 and which produces a pulse voltage in a repetitive period proportional to an input voltage from a low-pass filter circuit 15 and which functions to operate flip-flop FF1 as a trigger pulse. Transistors Q2 and Q3 compose a motor drive circuit 17 for pulse motor PM, the resistors R7 and R8 designating base resistors for the transistors Q2 and Q3. Also a resistance series connector of resistor R3b and variable resistor VR2b are selected by switch SW1 in the circuit 16. This selection is intended to select a conversion factor of the circuit 16, and stated more concretely, the time constant of a Miller integration circuit constructed to include amplifier A2 is determined by CR circuit between this selected resistance connector and condenser C3. The selection of this resistance series connector is effected before starting of X-ray photographing. The comparator circuit compares a reference voltage source E1 with this integration output by a conmparator A3 and includes resistors R4 and R5 and condenser C4.

Figure 4:
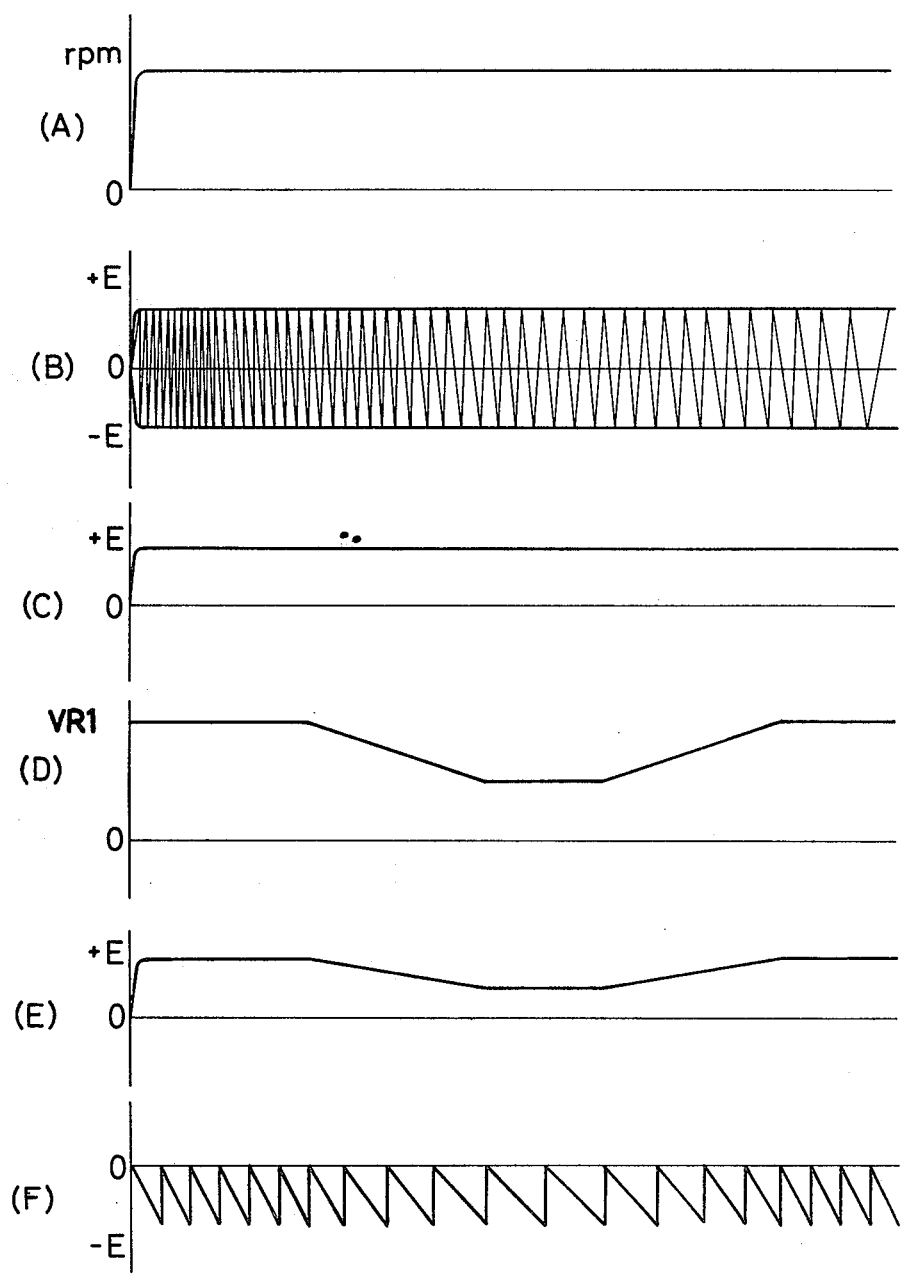
FIG. 4 is a signal waveform diagram for each part in FIG. 3 for explanation of the operation.
Figure 4:
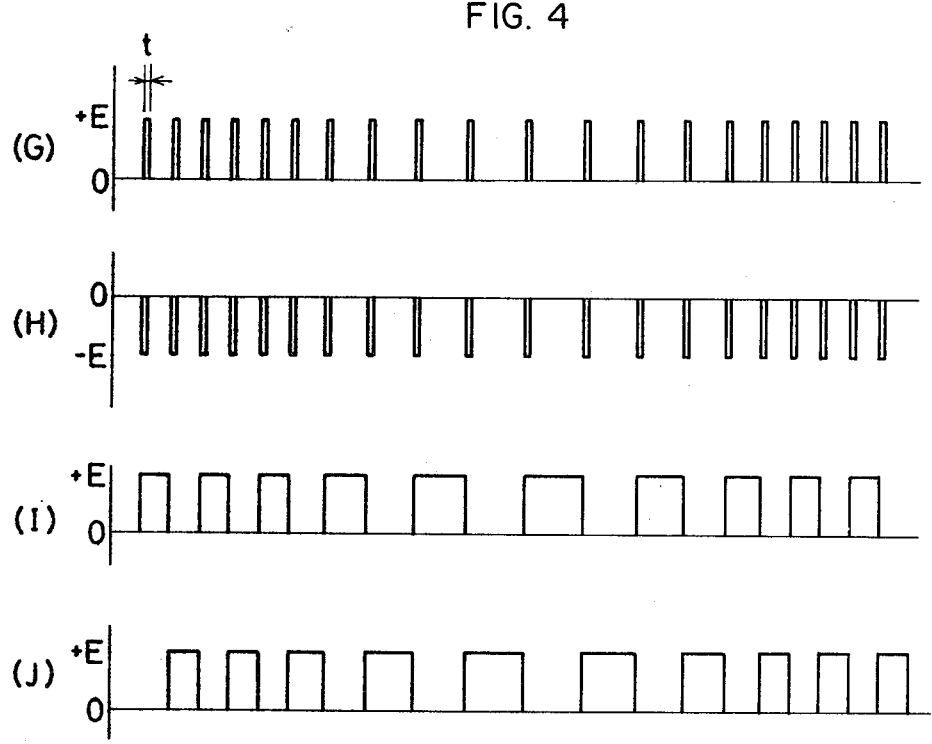

Next, referring to the operation of the circuitry shown in FIG. 3 in conjunction with the signal waveform diagram in FIG. 4, the motor IM is actuated and rotatably controlled by a drive circuit (not shown). The number of rotations of this motor IM is derived by the tachogenerator G in the form of AC voltage proportional to the number of rotations in FIG. 4(B), and after the AC voltage thus derived has been changed into a pulse (FIG. 4(4)) by the rectifier RFD, the pulse obtained passes from the variable resistor VR1 to and through the low-pass filter circuit 15 to thereby have its high frequency AC component damped. Accordingly, if the resistance value of the variable resistor VR1 is constant, DC voltage proportional to the number of rotations of motor is derived in the form of output of the low-pass filter circuit 15 (as a matter of fact, because the resistance value is continuously changed, the output of the low-pass filter circuit 15 is changed as shown in FIG. 4(E)). The output of the low-pass filter circuit 15 is supplied to an amplifier A2 through a resistor R3a and variable resistor VR2a or resistor R3b and variable resistor VR2b selected by switch SW1 and is integrated, and generates a saw tooth wave (FIG. 4(F)) of frequency proportional to the above output voltage, and furthermore comparison is made by the comparator A3 between Miller integration circuit output voltage and reference voltage source E1. And when integration circuit output exceeds reference voltage, the comparator A2 outputs positive output voltage, and this voltage is fed back to the Miller integration circuit through resistor R6 and diode D1, and transistor Q1 is biased and energized and discharges a condenser C3, and Miller integration output is instantly reduced to zero. The output voltage of comparator A2 is held at the same voltage for a certain time t as in FIG. 4(G) by the time constant determined by condenser C4 and resistor R5 and subsequently thereto the output is stopped to deenergize transistor Q1, with the result that integration operation is again started. A positive pulse synchronous with the saw tooth wave as shown in FIG. 4(G) is outputted by this repeated operation from the comparator A3, and this positive pulse is led to a buffer amplifier A4 where the positive pulse is reversed to a negative pulse and flip-flop FF1 is triggered by the buffer amplifier output (FIG. 4(H)). In the flip-flop FF1, the pulse output shown in FIGS. 4(I) and 4(J) is alternately produced each time the flip-flop FF1 is triggered by the buffer amplifier output (FIG. 4(H)) to thereby energize transistors Q2 and Q3 of motor drive circuit 17 alternately and to drive the pulse motor PM by the drive source E2 of the motor PM to turn the motor PM and feed the X-ray film. At this time, the pulse intervals of the buffer amplifier output for energizing the flip-flop FF1 are in a synchronized relation with respect to the saw tooth wave (FIG. 4(F)) and accordingly the pulse intervals are proportional to the number of rotations of the motor IM, and in consequence, the output intervals of the flip-flop FF1 triggered by the output of the buffer amplifier are also brought into proportion to the number of rotations of the motor IM. When the rotating travelling speed of the X-ray generator 5 is constant, the feed speed of the X-ray film is also made constant, and if the travelling speed of the X-ray generator is increased, the feed speed of the X-ray film increases correspondingly, and conversely if the travelling speed of the generator 5 is decreased, the feed speed of the X-ray film is decreased correspondingly thereto. Synchronous control in the invention is effected in such a manner.

But in the invention, to detect the X-ray irradiation position as an electrical signal as described for example in FIGS. 1 and 2, a cam plate 11 is fixed to the top of a receiving plate 9 and a plunger 13 is urged by a spring member 14 against the circumferential cam face 12 of the cam plate 11, and the variable resistor VR1 is interlocked with this plunger 13, so that when the rotary arm 4 begins to move in accordance with the starting of X-ray photographing, the plunger 13 is expanded and contracted in accordance with the sliding of the plunger 13 along the circumferential cam face 12 and the resistance value or the variable resistor VR1 sequentially changes as shown for example in FIG. 4(D). Accordingly, the output voltage of the low-pass filter circuit 15 is also changed as shown in FIG. 4(H), and henceforth the DC voltage-pulse converter circuit 16 also operates correspondingly to this voltage change, with the result that the number of rotations of motor PM is brought out of synchronization with the number of rotations of motor IM and is varied by change in the resistance value of the variable resistor VR1. In short, an input signal entirely different from the input signal derived from the number of rotations of motor IM is inputted into the film feed motor drive control circuit A to thereby change the resistance value of the variable resistor VR1 and to change the transfer constant of the circuit A, with the result that the number of rotations of the motor PM is amplified and controlled independent of the number of the motor IM. For example, even if the moving speed of the X-ray generator 5 is set at a constant speed (namely, the number of rotations of motor IM is constant), the feed speed of X-ray film can independently be increased or decreased by the control of the variable resistor VR1 made by the cam plate 11. Since the control of the variable resistor VR1 by the cam plate 11, in this case, is effected in accordance with the rotation of the rotary arm 4, the the resistance value of the variable resistor VR1 corresponds to the X-ray beam irradiation position the generator 5 takes with respect to the dental arch when the generator 5 moves around the dental arch. In other words, the X-ray beam irradiation position the generator takes with respect to the dental arch is changed and detected moment by moment and continuously as a change in resistance value of variable resistor VR1 in accordance with the rotating travel of the X-ray generator. In this manner, in the embodiment illustrated, the X-ray beam irradiation position is detected by the change in the resistance value of the variable resistor VR1 to thereby vary the transfer constant of the circuit A, and accordingly when the X-ray generator 5 reaches the desired specified position or specified area of the dental arch, this arrival of the generator is detected by the variable resistor VR1 to vary the number of rotations of motor PM, increase or decrease the X-ray film feed speed, increase magnification factor in the tooth in the above specified position or specified region with respect to teeth in the other regions or operate reversely. Furthermore, the shape of the cam plate 11 may optionally be changed, and this selection of the cam plate makes it possible to facilitate the change in the above specified position or the specified area and to increase or decrease the magnification factor.

As apparent from the description so far given, this invention is beneficial in that a film feed motor is mounted independent of the rotary arm drive motor, both motors are electrically connected to each other and the X-ray beam irradiation position in the process of rotation of the rotary arm is derived as an electrical signal and the number of rotations of the film feed is controlled independent of the rotary arm drive motor and accordingly the magnification factor of the specified position or specified area of the dental arch can be simply varied.

It is to be understood that the invention is not limited in its application to the details of construction and arrangement of parts illustrated in the accompanying drawings, since the invention is capable of other embodiments and of being practiced or carried out in various ways. Also, it is to be understood that the phraseology of terminology employed herein is for the purpose of description and not of limitation.

I claim:

1. An X-ray film feed speed control system in a dental radiographic apparatus for photographing the entire jaws, said apparatus including an X-ray generator, a horizontal rotary arm holding an X-ray film cassette having an X-ray film therein and a rotary arm holding an X-ray film cassette having an X-ray film therein and a rotary arm drive motor for rotatingly moving said rotary arm, said generator and said motor being provided respectively at one end of said arm and at the other end thereof with an object interposed therebetween, said apparatus being designed to make a tomogram of the entire jaws of the object by actuating said arm drive motor and simultaneously feeding the X-ray film, said control system comprising:

providing a film feed motor for said X-ray film feed in a drive control circuit for the film feed motor independent of said rotary arm drive motor;

converting the number of rotations of said rotary arm drive motor into an electrical signal;

supplying the electrical signal thus converted to said X-ray film feed motor drive control circuit in the form of a drive signal;

detecting an X-ray beam irradiation position of said X-ray generator rotating around the dental arch as an electrical signal with respect to the dental arch of said object; and controlling said drive signal supplied by said detected electrical signal to said drive control circuit, thereby automatically and variably controlling said X-ray film feed motor through the number of rotations responding to the detected electrical signal while said horizontal rotary arm is being rotated.

2. A system according to claim 1, wherein said method of converting the number of rotations of said rotary arm drive motor is a method of converting the number of rotations of the rotary arm drive motor into an electromotive force proportional to the number of rotations of the rotary arm drive motor.

3. A system according to claim 1, wherein said rotary arm drive motor is an induction motor.

4. A system according to claim 1, wherein said film feed motor is a pulse-driven motor.

5. A system according to claim 2, wherein said film feed drive control circuit is a circuit for pulse-driving a film feed motor by outputting a pulse signal having a repetitive period variable correspondingly to the AC electromotive force generated in response to the number of rotations of said rotary arm drive motor.

6. A system according to claim 2, wherein said method of converting the number of rotations of said rotary drive motor is carried out by connecting a tachogenerator to the rotary drive motor.

7. A system according to claims 3 or 4, wherein said pulse drive motor is a two-phase pulse motor.

8. A system according to claim 1, wherein said method of detecting the X-ray beam irradiation position of said X-ray generator is carried out by changing a variable resistance value in accordance with the rotation of said rotary arm by means of a cam plate fixed to the rotary arm.

9. A system according to claim 1, wherein said film feed motor is a pulse-driven motor and said method of converting the number of rotations of said arm drive motor into an electrical signal is carried out by means of a tachogenerator connected to the rotary arm drive motor and said method of detecting the X-ray beam irradiation position of the X-ray generator and substituting the irradiation position for an electrical signal and further controlling said drive signal is carried out by changing the variable resistance value by means of the cam plate fixed to said horizontal rotary arm.

10. A system according to claim 5, wherein said film feed drive control circuit comprises a rectifier circuit, a DC voltage-pulse converter circuit and a drive circuit for energizing said film feed motor.

* * * * *